US007759358B2

(12) United States Patent
Crooks et al.

(10) Patent No.: US 7,759,358 B2
(45) Date of Patent: Jul. 20, 2010

(54) ORAL BIOAVAILABLE PRODRUGS (76) Inventors: Peter A. Crooks, 409 W. Brannon Rd., Nicholasville, KY (US) 40356; Mohamed Omer Hamad, 900 Calypso Breeze Dr., Lexington, KY (US) 40515; Audra Lynn Stinchcomb, 4080 Weber Way, Lexington, KY (US) 40514

( * ) Notice: Subject to any disclaimer, the term of this patent is extended or adjusted under 35 U.S.C. 154(b) by 709 days.

(21) Appl. No.: 10/897,428

(22) Filed: Jul. 23, 2004

(65) Prior Publication Data
US 2005/0154002 A1 Jul. 14, 2005

Related U.S. Application Data (60) Provisional application No. 60/489,103, filed on Jul. 23, 2003.

(51) Int. Cl.
*A61K 31/485* (2006.01)
*C07D 489/09* (2006.01)
(52) U.S. Cl. .................................. 514/282; 546/45
(58) Field of Classification Search ................. 514/282; 546/45
See application file for complete search history.

(56) References Cited

U.S. PATENT DOCUMENTS 3,203,980 A * 8/1965 Swintosky ................... 558/272
3,372,181 A * 3/1968 Swintosky ................... 558/265
4,673,679 A 6/1987 Aungst et al.
6,225,321 B1 5/2001 Hu et al.
6,649,652 B2 11/2003 Boykin et al.

FOREIGN PATENT DOCUMENTS

EP 1149836 * 10/2001
EP 1 243 276 A1 9/2002
EP 1243276 * 9/2002

OTHER PUBLICATIONS

Bennett et al. "Biodegradable polymeric . . . " J. Controlled release v.16, p. 43-52 (1991).*
Dripps "Anethesia" CA49:79761 (1955).*
Nelson "Trichloroethylene: possible opioid involvement" CA 109:18490 (1988).*
Burce et al. "Quantitative determination . . . " J. Chromatography v.137, p. 323-332 (1977).*
Hansen et al. "Enhanced transdermal . . . " CA 117:239647 (1992).*
Swintosky et al. "Carbonate prodrugs . . . " J. Pharm. Sciences v.55, p. 992 (1966).*
Bundgaard Design of prodrugs p. 3-5 (1986).*
Flippen et al. "X-ray crystal structure . . . " CA 122:227373 (1995).*
Hammell, Dana C., et al., "A duplex "Gemini" prodrug of naltrexon for the transdermal delivery" *Journal of Controlled Release*, Mar. 20, 2004, 284-290, Elsevier B.V., Lexington, KY.
Sinchcomb, Audra L, et al., "Straight-Chain Naltrexone Ester Prodrugs: Diffusion and Concurrent Esterase Biotransformation in Human Skin", Journal of Pharmaceutical Sciences, Dec. 2002 vol. 91, No. 12 Wiley-Liss, Inc. and the American Pharmaceutical Association.
Database Caplus on STN (Columbus, OH, USA) No. 135:352654, 'inhibition of alzheimer's disease beta-amyloid aggregation . . . ' abstract, DeFelice et al., 2001.
Database Caplus on STN (Columbus, OH, USA) No. 103:81144, 'Hydroxyanisole: the current status' (1985).
Database Caplus on STN (Columbus, OH, USA) No. 137 'Elongated and multiple spacers . . . ' abstract (2002) DeGroot at al.
Database Caplus on STN (Columbus, OH, USA) No. 119:125020 'Skin-dipigmenting prodrus of hydroquinone' abstract (1993) Nudelman et al.
Database Caplus on STN (Columbus, OH, USA) No. 141:199470 "Synthesis and biological evaluation of bis and monocarbonate prodrugs of 10-hydrocycamptothesins" abstract (2004).

* cited by examiner

*Primary Examiner*—Celia Chang
(74) *Attorney, Agent, or Firm*—McDermott Will & Emery LLP (57) ABSTRACT The invention is directed to forming duplex prodrugs that provide significant increase in the transdermal flux of drugs across human skin. The prodrugs are prepared by reacting a drug that can form an ester moiety with phosgene to form a carbonate. The drug can be an opiate or an opiate antagonist. When in contact with human skin, the duplex drug is biotransformed by enzymes or by hydrolysis into two drug molecules.

10 Claims, 2 Drawing Sheets

ORAL BIOAVAILABLE PRODRUGS

CROSS REFERENCE TO RELATED APPLICATION

This application claims the benefit of priority of U.S. Provisional Application No. 60/489,103 filed Jul. 23, 2003, which is incorporated herein by reference.

A portion of this invention was made with U.S. Government support under a grant from the National Institutes of Health under NIH Grant R01AA013853. The Government may have certain rights in this invention.

FIELD OF THE INVENTION

This invention relates to novel prodrugs, and more particularly to novel duplex prodrugs which increase the bioavailability of the drugs.

BACKGROUND OF THE INVENTION

Transdermal delivery is desirable to reduce the side effects associated with the oral administration of a drug such as abdominal pain, nausea and vomiting and also to offer a patient freedom from injections and surgical implantations. Transdermal delivery is provided through a transdermal patch which provides sustained release of a drug for about a week. Transmittal delivery also bypasses the significant metabolism associated with oral administration of the drug.

The present invention is directed to novel duplex prodrugs that provide a significant increase in the transdermal flux of such drugs across human skin, as compared to the basic drug. The prodrug of the present invention may increase the transdermal drug delivery rate either by a solubility improvement or by a permeability improvement, or a combination of both.

SUMMARY OF THE INVENTION

In one aspect, the present invention provides a novel duplex prodrug, which improves the oral bioavailability of the drugs. The term "duplex prodrug" as used in the specification and claims means two molecules of a drug are joined together by chemical bonding. The term "drug" as used to describe this invention means a substance used as a medication or in the preparation of a medication, but it does not include an alcohol such as ethanol. The drug molecule must have one or more connecting bonds or groups. It is preferred that the drug has a hydroxyl moiety that can be converted into an ester moiety. On introduction of the duplex drug into the body, the chemical bond is disrupted and the drug becomes is available for its intended purpose.

The present invention provides a duplex prodrug for transdermal delivery comprising a carbonate having the following formula:

wherein X—OH is a drug as defined above and X—O— is the ester moiety of the drug. It is preferred that the drug is an opiate. Naltrexone (NTX) and the resulting prodrug (NTX-NTX) are preferred embodiments.

The present invention further provides for a method of forming a prodrug carbonate by providing a solution containing a drug base and mixing the solution with phosgene to form the carbonate.

The present invention still further provides for a method for delivery of a drug by and biotransforming the duplex drug into two active drug molecules by hydrolysis or enzymes. The term "biotransforming" as used with respect to the description of the invention means using water or enzymes to cause the duplex prodrug to be transformed into two active drug molecules.

BRIEF REFERENCE TO THE DRAWINGS

Reference is now made to the drawings accompanying the application wherein.

DESCRIPTION OF THE INVENTION

According to the present invention, it has been discovered that the novel duplex prodrugs of the invention provide a significant increase in the transdermal flux of such drugs across human skin, as compared to the basic drug. This extremely unique prodrug may be increasing the transdermal drug delivery rate either by a solubility improvement or by a permeability improvement, or a combination of both. Opiate drugs are especially preferred.

The invention is directed to a duplex prodrug for transdermal delivery comprising a carbonate having the following formula:

wherein X—OH is a drug as defined above and X—O— is the ester moiety of the drug. The drug is selected from the group consisting of Naltrexone, Buprenorphine, Butorphanol, Codeine, Dihydrocodeine, Dihydromorphine, Ethymorphine, Hydromorphone, Levallorphan, Levorphanol, Nalbuphine, Nalmefene, Nalorphine, Naloxone, 6-β-Naltrexol, Phenazocine, Pholcodine, or 6-α-Naltrexol. In a method for transdermal delivery of the drug, the steps comprise contacting a section of human skin with the duplex prodrug carbonate and biotransforming the prodrug into two drugs by skin enzymes or by hydrolyzing the carbonate in the skin. A transdermal patch comprising a suitable substrate and a layer of the duplex carbonate can be employed to deliver the duplex prodrug to the skin.

Due to the novel design of this duplex prodrug, any toxicities associated with this compound should be non-existent. For example, when a duplex prodrug of Naltrexone (NTX) is cleaved, only NTX and carbon dioxide (carbonic acid) are released. NTX has a well established safety profile in humans. The theory of the duplex prodrug can be expanded to encompass transdermal delivery of many other drugs. Opiates and opiate antagonists are preferred, however, any other drug classes with the appropriate chemistry, for example a drug that can form an ester moiety, can be used. The duplex prodrug can also be used to enhance drug delivery by other routes, including but not limited to: intravenous, oral, buccal, sublingual, topical creams, subdermal, as a sustained release depot, ophthalmic, intranasal, aural, by inhalation, rectal, and vaginal.

NTX is an opioid antagonist and has the following formula:

NTX

It is currently used to help maintain opioid addicts in a drug-free state. Most recently, NTX has been indicated as an adjunct in the treatment of alcohol dependence, as well as reported to reduce alcohol craving in certain alcoholic populations. Naltrexone hydrochloride is currently commercially available in the United States as a 50-mg oral tablet (ReVia™). NTX undergoes extensive first-pass metabolism and has oral bioavailability estimates ranging from five to forty percent. NTX is also a hepatotoxin that has the capacity to cause dose-related hepatocellular injury. This hepatotoxicity limits dosage increases in those addicts who may benefit from more than a 50 mg per day oral dose. Transdermal delivery would circumvent these liver-related problems by allowing lower doses to be used, because first-pass metabolism is bypassed. Certainly, the ability to decrease the drug dosage would benefit the already hepato-compromised alcoholic or narcotic addict. Many of the adverse effects seen with NTX oral therapy (abdominal pain, nausea, and vomiting) may also be reduced by transdermal therapy. Compliance, the major problem with addict recovery pharmacological intervention, is likely improved when side effects are reduced and drug doses are adequate to reduce craving. In fact, compliance has been a critical issue in the response of alcoholics to naltrexone therapy in recent clinical trials. This disclosure identifies a novel analogue of NTX which we believe will enhance the therapeutic value of NTX by reducing side effects and improving addict compliance with transdermal delivery.

NTX itself does not have the essential physicochemical properties that would allow a therapeutic dose of the drug to cross the human skin barrier. In this invention, a novel duplex prodrug of NTX has been synthesized as follows:

In a similar manner, other drug bases can be employed to form duplex prodrugs using the synthesis technique of the present invention. The novel duplex drug design of the present invention includes the following structural entities 1-17 illustrated below. These structures all incorporate active drug moieties. As described above, like the naltrexone duplex prodrug, NTX-NTX, these novel duplex structures afford improved bioavailability of the parent drug, not only via the transdermal route, but also via other delivery routes such as those previously mentioned.

1

Duplex Prodrug of Buprenorphine

-continued

Duplex Prodrug of Butorphanol

Duplex Prodrug of Codeine

Duplex Prodrug of Dihydrocodeine

Duplex Prodrugs of Dihydromorphine

Duplex Prodrug of Ethylmorphine

-continued

Duplex Prodrug of Hydromorphone

7

Duplex Prodrug of Levallorphan

8

Duplex Prodrug of Levorphanol

9

10a

-continued

10b

10c

Duplex Prodrugs of Nalbuphine

11

Duplex Prodrug of Nalmefene

12a

-continued

Duplex Prodrugs of Nalorphine

Duplex Prodrug of Naloxone

Duplex Prodrugs of 6-β-Naltrexol

Duplex Prodrug of Phenazocine

Duplex Prodrug of Pholcodine

Duplex Prodrugs of 6-α-Naltrexol

The duplex prodrugs of the present invention are synthesized by reacting a drug with phosgene resulting in two drug molecules bonded together by a carbonate ester linkage. The duplex prodrug can be delivered to a patient transdermally, intravenously, orally, buccally, sublingually, by topical creams, subdermally, as a sustained release depot, ophthalmically, intranasally, aurally, by inhalation, rectally or vaginally. After delivery, the prodrug is biotransformed by hydrolysis or enzymes into two active drug molecules.

The duplex prodrug of NTX provides an unexpected increase of NTX maximum flux rate across human skin. Similar results would be expected for other duplex prodrugs set forth above. Extensive conversion of this duplex prodrug to NTX occurred in the viable skin layers. The success of this duplex prodrug has been evaluated by in vitro diffusion studies with human skin, to determine the level of NTX transdermal delivery enhancement. In the present invention, the viability of the in vitro experimental conditions have been optimized. It is critical to use a viable model to assess the performance of a prodrug that undergoes biotransformation in the skin. Without the added mechanism of prodrug biotransformation in the passive diffusion experiment, the true effect of metabolic rates on subsequent active drug (NTX) transdermal delivery rates would be neglected. Several researchers have suggested that prodrug biotransformation rates are critical in predicting active (parent) drug transdermal flux.

Prodrug strategies to improve NTX's oral bioavailability and mask its bitter taste for buccal delivery have been reported in the literature, but no information exists about the transdermal use of these prodrugs. The goal of the oral bioavailability study was to block the 3-phenolic hydroxyl group of naltrexone in order to prevent conjugation during absorption, as opposed to increasing permeability. Ester prodrugs successfully increase the oral bioavailability and mask the bitter taste of naltrexone. Some researchers have suggested that a transdermal penetration enhancer formulation with naltrexone can achieve a desired plasma level in humans. A major advantage of using transdermal prodrugs with prompt biotransformation is that their skin irritation and allergenic potential should only mirror the profile of the active drug, without the possible added toxicities of penetration enhancers.

In a particular embodiment of the present invention, the synthesis and evaluation of a duplex prodrug of naltrexone, NTX-NTX is described below. The analogous duplex prodrugs described above can prepared using the same techniques as the NTX-NTX process of preparation.

EXAMPLE

Synthesis of 3,3'-Di-(N-cyclopropylmethyl-4,5-epoxy-14-hydroxy-morphinan-6-one-3-yl) Carbonate (NTX-NTX)

NTX base was purchased from Mallinckrodt Inc., St. Louis, Mo. The high-pressure liquid chromatography (HPLC) assay used was developed from the methods of Hussain et al. (reference 15 at the end of this disclosure). The samples were analyzed using a Perkin-Elmer Series 200 Autosampler, Pump, Column Oven, and a 785A UV/VIS Detector with Turbochrom Professional Version 4.1 Software. A Brownlee Valueline C-18 reversed-phase Spheri-5 µm column (220×4.6 mm) with a C-18 reversed phase 7 µm guard column (15×3.2 mm) was used with the UV/VIS Detector set at a wavelength of 215 nm. The mobile phase was comprised of acetonitrile:0.1% trifluoroacetic acid (TFA) with 1 g/L 1-heptane sulfonic acid, sodium salt and used at a 70:30 ratio. The 0.1% TFA was adjusted with triethylamine (TEA) to a pH of 3.0. The flow rate of the mobile phase was 1.5 mL/min with 100 µL sample injections. Standards were analyzed with each set of diffusion samples and exhibited excellent linearity over the entire concentration range employed in the assays. The sensitivity of the assay was 50 ng/mL and 200 ng/mL for NTX and NTX-NTX, respectively.

Diffusion samples that were collected with the fraction collector were processed through solid-phase extraction cartridges (30 mg 1 cc Oasis HLB, Waters Corp., Milford, Mass.). The Prep-Torr extraction cartridge apparatus was cleaned with 5 mL of methanol per needle. The cartridges with adaptors were inserted into the Prep-Torr, and preconditioned with 1 mL of methanol and then 1 mL of nanopure water. Five milliliters of the samples were run through the cartridges. The cartridges were washed with 1 mL of 5% methanol/95% water solution. Samples were eluted with 1.1 mL of acetonitrile and placed in HPLC vials for analysis.

A mixture of 1.5 ml of a solution of phosgene ($COCl_2$, 2.8 mmole, 20% w/w in toluene) and 2 ml of tetrahydrofuran (THF) was cooled to 0° C. in an ice-bath. To this stirred mixture was added a solution of naltrexone (120 mg, 0.35 mmole) and triethylamine (50 µl, 0.35 mmole) in 3.0 ml of THF. After stirring for 14 hours, the excess phosgene and the solvents were removed in a stream of nitrogen. The resulting residue was dissolved in methylene chloride and washed with 10% aqueous sodium carbonate (2×20 ml), then water (20 ml). Then the organic solution was separated and dried over anhydrous potassium carbonate and reduced to a small volume under reduced pressure. The desired product was precipitated by trituration with excess pentane. The resulting solid was filtered at the pump, washed with diethyl ether and air-dried to afford a white powder: m.p. 140-142° C.; $t_R$ 5.25 minutes [reverse phase HPLC (Symmetry $C_{18}$ column, 3.5 µm, 2.1 mm×10 cm), buffer: acetonitrile containing 5% 2 mM ammonium acetate: 2 mM ammonium acetate containing 5% acetonitrile, 4:1, flow rate 0.25 mL/min]; FT-IR 3,337, 3,077, 2,999, 2,929, 2,827, 2,362, 1,786, 1728, and 1,626 $cm^{-1}$. MS (Moldi-Toft) m/z 709 ($M^+$, base peak), 415, 371, 355, 346. NMR. The data is set forth in Tables 1 and 2.

TABLE 1

Chemical Shifts and Coupling Constants in the Proton Magnetic Resonance Spectrum of NTX—NTX.

| | Chemical shifts (δ, ppm from TMS) | Splitting pattern | Coupling constants (in Hz) | |
|---|---|---|---|---|
| H-1 | 7.075 | doublet | J(1, 2) | 8.4 |
| H-2 | 6.898 | d | J(2, 1) | 8.1 |
| H-5 | 4.727 | s | | |
| H-7 | 2.863 | d, d | J(7, 7') | 12.0 |
| | | | J(7, 8) | 4.5 |
| H-7' | 2.393 | d, t | J(7', 7) | 12.0 |
| | | | J(7', 8) | 12.0 |
| | | | J(7', 8') | 5.4 |
| H-8 | 2.090 | d, t | J(8, 8') | 12.0 |
| | | | J(8, 7) | 3.6 |
| | | | J(8, 7') | 12.0 |
| H-8' | 1576 | d, d | J(8', 8) | 12.0 |
| | | | J(8', 7') | 5.4 |
| H-9 | 3.208 | d | J(9, 10α) | 5.7 |
| H-10α | 2.622 | d, d | J(10α, 10β) | 18.6 |
| | | | J(10α, 9) | 5.7 |
| H-10β | 3.093 | d | J(10β, 10α) | 18.6 |
| H-15 | 1.644 | t, d | J(15, 15') | 13.8 |
| | | | J(15, 16) | 4.8 |
| | | | J(15, 16') | 3.0 |
| H-15' | 1.998 | d, t | J(15', 15) | 13.8 |
| | | | J(15', 16) | 13.8 |
| | | | J(15', 16') | 3.0 |
| H-16 | 3.024 | d, t | J(16, 16') | 14.7 |
| | | | J(16, 15) | 14.7 |
| | | | J(16, 15') | 4.8 |
| H-16' | 2.328 | t, d | J(16', 16) | 14.7 |
| | | | J(16', 15) | 3.0 |
| | | | J(16', 15') | 2.7 |
| H-17 | 2.410 | broad | | |
| H-17' | 2.395 | broad | | |
| H-18 | 0.850 | m | | |
| H-19 | 0.574 | m | | |
| H-19' | 0.158 | m | | |
| H-20 | 0.550 | m | | |
| H-20' | 0.142 | m | | |

TABLE 2

$^1H-^1H$ Coupling Values for NTX—NTX Coupling constants (in Hz)

| | |
|---|---|
| J(1, 2) | 8.4 |
| J(2, 1) | 8.1 |
| J(7, 7') | 12.0 |
| J(7, 8) | 4.5 |
| J(7', 7) | 12.0 |
| J(7', 8) | 12.0 |
| J(7', 8') | 5.4 |
| J(8, 8') | 12.0 |
| J(8, 7) | 3.6 |
| J(8, 7') | 12.0 |
| J(8', 8) | 12.0 |
| J(8', 7') | 5.4 |
| J(9, 10α) | 5.7 |
| J(10α, 10β) | 18.6 |
| J(10α, 9) | 5.7 |
| J(10β, 10α) | 18.6 |
| J(15, 15') | 13.8 |
| J(15, 16) | 4.8 |
| J(15, 16') | 3.0 |
| J(15', 15) | 13.8 |
| J(15', 16) | 13.8 |
| J(15', 16') | 3.0 |
| J(16, 16') | 14.7 |
| J(16, 15) | 14.7 |
| J(16, 15') | 4.8 |
| J(16', 16) | 14.7 |
| J(16', 15) | 3.0 |
| J(16', 15') | 2.7 |

In vitro diffusion studies were conducted using human skin harvested during abdominal reduction surgery. Skin sections were obtained by using a Padgett dermatome set to 250 microns, and then were frozen at −20° C. until the time of the experiment. A PermeGear flow-through (In-Line, Riegelsville, Pa.) diffusion cell system was used for the diffusion studies. Data was collected utilizing three different specimens of frozen human tissue from three different donors. The human tissues had been frozen from two to five months. Three diffusion cells were used for NTX and four cells were used for NTX-NTX. A receiver buffer of HEPES-buffered Hank's balanced salts solution with gentamicin at pH of 7.3-7.4 was collected at a flow rate of 1.1 mL/h. A saturated NTX or NTX-NTX solution in light mineral oil was applied to the skin cells. Each cell received 0.25 mL of the respective drug solution. Samples were collected in six hour increments for 48 hours. After a six hour sample was obtained, they were stored at 4° C. until solid phase extraction processing. Skin cells were kept at 32° C. with a circulating water bath set to 39° C.

The diffusion data were plotted as the cumulative quantity of NTX equivalents collected in the receiver cell as a function of time. The flux value for a given experiment was computed from Fick's First Law of diffusion:

$$\frac{1}{A}\left(\frac{dM}{dt}\right) = J_s = K_p \Delta C$$

where $J_s$ is the steady-state flux, M is the cumulative amount of intact drug permeating the skin, A is the area of the cell (0.95 cm$^2$), $K_p$ is the effective permeability coefficient in cm/h, and $\Delta C$ is the difference in concentration of NTX or NTX-NTX in the donor and receiver. Buildup in the receiver cell was kept to a minimum throughout the studies.

Figure 1:
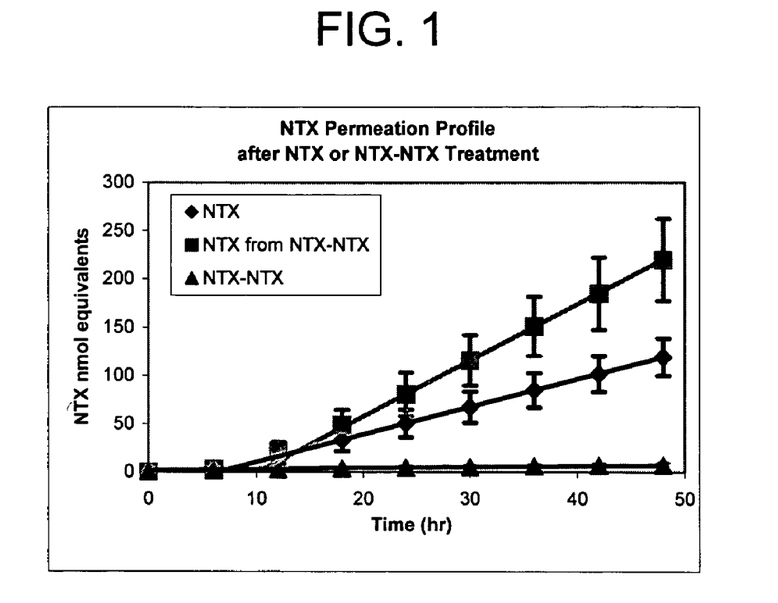
FIG. 1 shows a permeation profile for the diffusion of Naltrexone and the Naltrexone prodrug in permeation studies.

NTX was hydrolyzed in the skin and appeared as NTX in the receiver collection. The total amounts of NTX that absorbed through the skin and into the receiver from NTX and NTX-NTX were used in the data analysis. The NTX permeation data is shown in FIG. 1 which shows representative permeation profiles for the diffusion of NTX and NTX-NTX from saturated solutions through human skin at 32° C. Data represent the mean±standard deviation of the nine skin cells with NTX and the twelve skin cells with NTX-NTX. Three individual human donor skin tissues were used. Due to the high variability of human skin, NTX was used with each experiment as a control. The results are reported in NTX nmol equivalents because the NTX-NTX duplex contains two molecules of NTX. Approximately 4% of the NTX flux was from the intact NTX-NTX prodrug, and 96% was NTX originating from the hydrolysis of NTX-NTX.

The concentration of NTX and NTX-NTX in the skin was determined after the 48 hour experiment was completed. Cells were taken apart and a notation was made regarding presence of drug solution. The skin tissue was rinsed with filtered water and blotted with a paper towel. The tissue was tape stripped twice to remove surface drug. The area of skin with drug contact was cut out, chopped into tiny pieces, and placed in a pre-weighed scintillation vial. The vial was weighed to calculate the mass of the skin. Ten mL of acetonitrile was added to the vial and parafilm was placed around the lid. The vials were vortexed, sonicated for 10 min, and placed in a shaker overnight. The following day, a 1 mL sample was obtained from the vials and placed in HPLC vials for analysis. The results were reported as micromole of NTX equivalent per gram of wet tissue weight.

Figure 2:
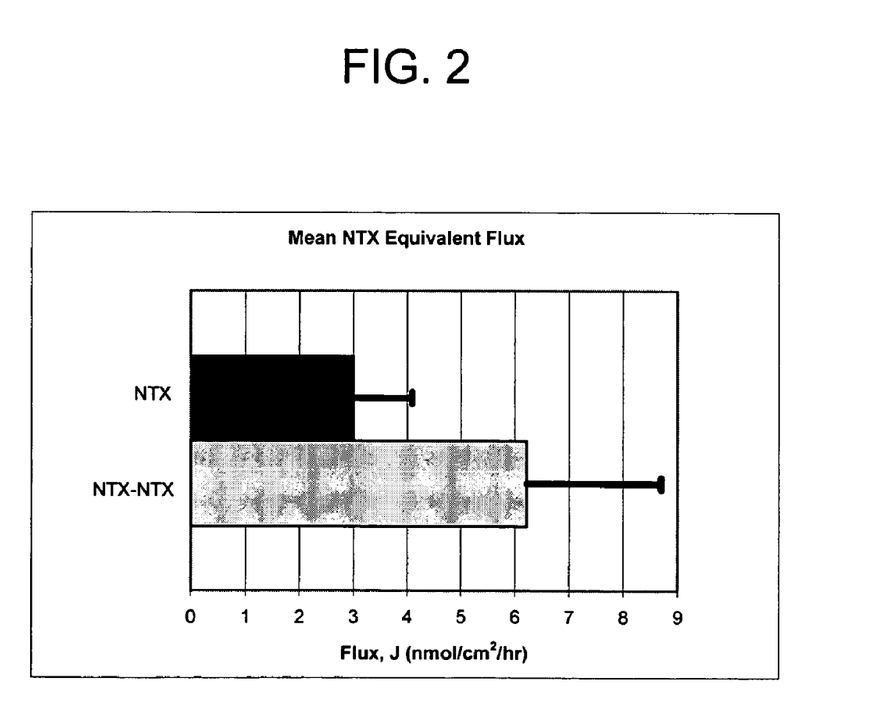
FIG. 2 shows in vitro Naltrexone flux from Naltrexone and the Naltrexone prodrug.

FIG. 2 shows data for in vitro NTX flux from NTX and NTX-NTX. The data represents the mean±standard deviation of the nine cells with NTX and the twelve cells of NTX-NTX. Three individual human donor skin tissues were used. A paired Student's t-test showed a significant difference between the means (p<0.05).

Figure 3:
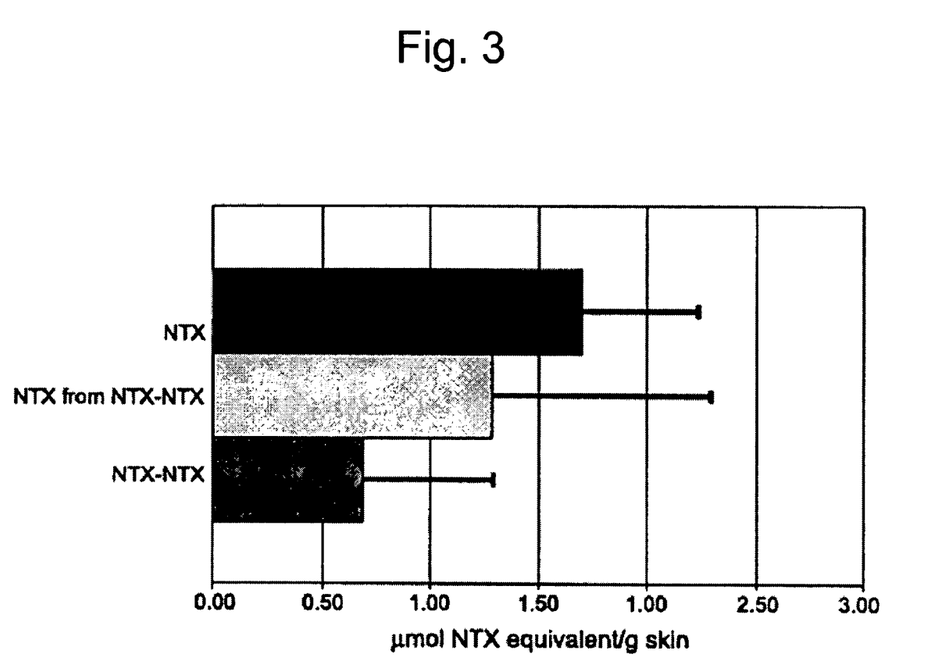
FIG. 3 shows representative drug concentrations of Naltrexone and the Naltrexone prodrug in the skin during a diffusion study.

FIG. 3 shows representative drug concentrations of NTX and NTX-NTX in the skin after a 48 hour diffusion study. The results are reported on a NTX equivalent because of the structure of the NTX-NTX duplex drug. FIG. 3 shows the NTX equivalent skin concentrations after treatment with NTX base (black bar), and after treatment with NTX-NTX (light grey and dark grey bars). No significant difference in total NTX equivalent was found between the NTX-treated skin and the NTX-NTX-treated skin. However, significant bioconversion of NTX-NTX to NTX was observed in the skin, since 66% of the drug extracted from the NTX-NTX-treated skin was NTX at the end of the 48 hour study. Thus, a significant increase in drug concentration in the skin after NTX-NTX treatment, as compared to NTX treatment, corresponds with the significant increase in NTX equivalent flux provided by NTX-NTX.

The following literature references are hereby incorporated by reference:

1. Volpicelli J R, Alterman A I, Hayashida M 1992. Naltrexone in the treatment of alcohol dependence. Arch Gen Psychiatry 49: 876-880.
2. O'Malley S S, Jaffe A, Chang G, Schottenfeld R S, Meyer R, Rounsaville B 1992. Naltrexone and coping skills therapy for alcohol dependence: A controlled study. Arch Gen Psychiatry 49: 881-887.
3. O'Malley S S, Jaffe A J, Rode S, Rounsaville B J 1996. Experience of a "slip" among alcoholics treated with naltrexone or placebo. American Journal of Psychiatry 153: 281-283.
4. Gianoulakis C, de Wail J P, Thavundayil J 1996. Implication of the endogenous opioid system in excessive ethanol consumption. Alcohol 13: 19-23.

5. PDR Generics Second Edition. 1996. Medical Economics, New Jersey, p. 2229-2233.
6. O'Malley S S. 1995. Strategies to maximize the efficacy of naltrexone for alcohol dependence. In Onken, Blaine, Boren editors. NIDA Research Monograph 150, NIDA, Rockville, Md., p. 53-64.
7. Volpicelli J R, Rhines K C, Rhines J S 1997. Naltrexone and alcohol dependence. Role of subject compliance. Arch Gen Psychiatry 54: 737-743.
8. Litten R, Allen J 1998. Advances in the development of medications for alcoholism. Psychopharmacology 139: 20-33.
9. Collier S W, Sheikh N M, Sakr A, Lichtin J L, Stewart R F, Bronaugh R L 1989. Maintenance of skin viability during in vitro percutaneous absorption/metabolism studies. Toxicol Appl Pharmacol 99: 522-533.
10. Smith W M 1982. An inquiry into the mechanism of percutaneous absorption of hydrocortisone and its 21-n-alkyl esters. Dissertation, The University of Michigan.
11. Yu C D, Fox J L, Ho N F H, Higuchi W I 1979. Physical model evaluation of topical prodrug delivery-simultaneous transport and bioconversion of vidarabine-5'-valerate I: physical model development and II: parameter determinations. J Pharm Sci 68: 1341-1357.
12. Ando H Y, Ho N F H, Higuchi W I 1977. Skin as an active metabolizing barrier I: Theoretical analysis of topical bio-availability. J Pharm Sci 66: 1525-1528.
13. Tojo K, Fan L T 1981. Membrane moderated controlled release. Math Biosci 57: 279-300.
14. Ahmed S, Imai T, Otagiri M 1996. Evaluation of stereoselective transdermal transport and concurrent cutaneous hydrolysis of several ester prodrugs of propranolol: mechanism of stereoselective permeation. Pharm Res 13: 1524-1529.
15. Hussain M A, Koval C A, Myers M J, Shami E G, Shefter E 1987. Improvement of the oral bioavailability of naltrexone in dogs: A prodrug approach. J Pharm Sci 76: 356-358.
16. Hussain M A, Aungst B J, Koval C A, Shefter E 1988. Improved buccal delivery of opioid analgesics and antagonists with bitterless prodrugs. Pharm Res 5: 615-618.
17. Chen Y L, Chun L L, Enscore D J (Mar. 4, 1986). Transdermal therapeutic systems for the administration of naloxone, naltrexone, and nalbuphine. Alza U.S. Pat. No. 4,573,995.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalence thereof may be resorted to, falling within the scope of the invention claimed.

What is claimed is:

1. A prodrug having the following formula:

wherein X—O— and X—O are the same and are identically selected from the group consisting of Naltrexone, Buprenorphine, Codeine, Dihydrocodeine, Dihydromorphine, Hydromorphone, Nalbuphine, Nalmefene, Nalorphine, Naloxone, 6-β-Naltrexol, Pholcodine, and 6-α-Naltrexol.

2. A method of forming a prodrug comprising the steps of:
providing a solution containing an opiate of opiate antagonist having a hydroxyl moiety that can be converted into an ester,
mixing said solution with phosgene to form the carbonate, wherein the prodrug has the following formula and wherein X—O— and X—O are the same and are identically selected from the group consisting of Naltrexone, Buprenorphine, Codeine, Dihydrocodeine, Dihydromorphine, Hydromorphone, Nalbuphine, Nalmefene, Nalorphine, Naloxone, 6-β-Naltrexol, Pholcodine, and 6-α-Naltrexol.

3. The method of claim 2, further comprising the step of mixing said prodrug Carbonate with a transdermal carrier to form a transdermal composition.

4. A drug composition comprising the prodrug of claim 1 and a transdermal pharmaceutical carrier.

5. A transdermal patch comprising a substrate and a layer of the prodrug carbonate of claim 1.

6. The transdermal patch of claim 5, wherein the prodrug has the following formula:

7. A method of delivering to a patient a therapeutically effective amount of a drug through biotransformation of a prodrug having the following formula:

wherein X—O— and X—O are the same and are identically selected from the group consisting of Naltrexone, Buprenorphine, Codeine, Dihydrocodeine, Dihydromorphine, Hydromorphone, Nalbuphine, Nalmefene, Nalorphine, Naloxone, 6-β-Naltrexol, Pholcodine, and 6-α-Naltrexol.

8. The method of claim 7, wherein the drug is delivered transdermally, and the biotransformation is by hydrolysis.

9. The method of claim 7, wherein the drug is delivered transdermally, and the biotransformation is by enzymes.

10. The method of claim 7, wherein each of X—O and X—O is Naltrexone and the prodrug has the following formula:

* * * * *